US012773283B2

(12) United States Patent
Bonaric et al.

(10) Patent No.: US 12,773,283 B2
(45) Date of Patent: Oct. 27, 2026

(54) ELECTRICAL INTERFACE FOR SURGICAL ROBOT ARM

(71) Applicant: ORTHOSOFT ULC, Montreal (CA)

(72) Inventors: Patrice Bonaric, Saint Georges d'Orques (FR); Francisco Molina, Montpellier (FR); Mickael Soriano, Fabrègues (FR); Pierre Maillet, Mudaison (FR)

(73) Assignee: ORTHOSOFT ULC, Montreal (CA)

( * ) Notice: Subject to any disclaimer, the term of this patent is extended or adjusted under 35 U.S.C. 154(b) by 197 days.

(21) Appl. No.: 18/646,976

(22) Filed: Apr. 26, 2024

(65) Prior Publication Data

US 2024/0358453 A1 Oct. 31, 2024

Related U.S. Application Data

(60) Provisional application No. 63/498,665, filed on Apr. 27, 2023.

(51) Int. Cl.

| | |
|---|---|
| ***A61B 34/30*** | (2016.01) |
| ***A61B 90/35*** | (2016.01) |
| *A61B 34/20* | (2016.01) |

(52) U.S. Cl.

CPC .............. *A61B 34/30* (2016.02); *A61B 90/35* (2016.02); *A61B 2034/2057* (2016.02)

(58) Field of Classification Search

CPC ................ B25J 19/0025; B25J 19/0029; B25J 19/0033; B25J 15/04; B25J 15/0408

See application file for complete search history.

(56) References Cited

U.S. PATENT DOCUMENTS

| | | | | |
|---|---|---|---|---|
| 11,485,010 | B2 * | 11/2022 | Zimmer | B25J 9/08 |
| 2012/0190981 | A1 * | 7/2012 | Harris | A61B 5/150954 604/95.01 |
| 2020/0146754 | A1 | 5/2020 | Row et al. | |
| 2021/0093404 | A1 * | 4/2021 | Chappuis | A61B 34/74 |
| 2022/0249187 | A1 * | 8/2022 | Kallenberger | A61B 17/07207 |
| 2022/0361972 | A1 * | 11/2022 | Armand | A61B 34/76 |
| 2022/0398744 | A1 | 12/2022 | Couture et al. | |

FOREIGN PATENT DOCUMENTS

| | | | | |
|---|---|---|---|---|
| CN | 105640647 B * | 10/2018 | A61B 34/30 |
| DK | 201800225 A1 * | 12/2019 | F16B 9/09 |
| EP | 3847989 A1 * | 7/2021 | A61B 90/39 |
| EP | 4389050 | 6/2024 | |
| WO | 2016141378 | 9/2016 | |
| WO | WO-2022150802 A1 * | 7/2022 | B25J 15/0023 |

* cited by examiner

*Primary Examiner* — Bobby Rushing, Jr.

(74) *Attorney, Agent, or Firm* — NORTON ROSE FULBRIGHT CANADA LLP

(57) ABSTRACT

An interface for a robotic arm comprising: a body having a first axial face adapted to be connected to a distal face of a link of a robotic arm, a second axial face adapted to be connected to a proximal face of an end effector, the second axial face having a geometry differing from a geometry of the proximal face of the end effector so as to define a peripheral band in the second axial face, the peripheral band facing distally. A connection configuration is provided for the interface to be fixed to the link and for the end effector to be fixed to the interface. Circuitry is embedded in the body. At least one light source in the peripheral band, the at least one light source connected to the circuitry to produce light in a distal direction of the robotic arm.

21 Claims, 5 Drawing Sheets

ELECTRICAL INTERFACE FOR SURGICAL ROBOT ARM

CROSS-REFERENCE TO RELATED APPLICATION

The present application claims the priority of U.S. Patent Application No. 63/498,665, filed on Apr. 27, 2023 and incorporated herein by reference.

TECHNICAL FIELD

The present application relates to hardware components of surgical robot arms used in robotized computer-assisted surgery.

BACKGROUND OF THE ART

Robot arms have become prominent equipment in surgical rooms, often in assistance to operating staff. In a particular application, commonly but not exclusively used in orthopedic surgery, the robot arm supports instruments, e.g., known as guides, relative to a body part of a patient, while the operating staff such as a surgeon manipulates the tools using the guides to perform bone alterations. The characteristics of a robot arm, such as its stiffness and capacity to hold its position and orientation, combined with the precision of robot arm position tracking, may benefit the operating staff and the patient by contributing to the success of a surgical procedure.

Indeed, a primary advantage of surgery assisted by motorized robots is the precision. Usually, robotic surgery assistance systems use, among other things, calibrated mechanical instruments, laser optical systems. Since these instruments are installed at the end of the robot to obtain optimum precision, the patient registration operation can only be carried out before the surgical procedure. Accuracy may then rely on the ability to keep the patient and the robot perfectly still.

In robot assisted surgery, the surgical robot arms do not necessarily interact directly with the patient's body, but rather serve as a collaborative tool used to assist the operating staff. Nevertheless, it may be desired to increase the functionalities associated with such surgical robot arm, as its end effector is in close proximity to the surgical site and thus at a unique point of view thereof.

Moreover, some surgical robots are commonly used with a navigation system incorporating a camera. It is therefore possible to continuously monitor the position of the instruments, the robot stand and the patient. The navigation system is usually located at a distance of about a meter or more. Consequently, there may be an accumulation of errors that may be proportional to the distances, to the various changes of reference frames, to the cumulative calculation times.

SUMMARY

In accordance with a first aspect of the present disclosure, there is provided an interface for a robotic arm comprising: a body having a first axial face adapted to be connected to a distal face of a link of a robotic arm, a second axial face adapted to be connected to a proximal face of an end effector, the second axial face having a geometry differing from a geometry of the proximal face of the end effector so as to define a peripheral band in the second axial face, the peripheral band facing distally; a connection configuration for the interface to be fixed to the link and for the end effector to be fixed to the interface; circuitry embedded in the body; and at least one light source in the peripheral band, the at least one light source connected to the circuitry to produce light in a distal direction of the robotic arm.

Further in accordance with the first aspect, for instance, the peripheral band extends around the proximal face of the end effector for at least 270 degrees.

Still further in accordance with the first aspect, for instance, the peripheral band extends around the proximal face of the end effector for 360 degrees.

Still further in accordance with the first aspect, for instance, the interface has a plurality of the light source, at least one of the light sources being located in each quadrant of the peripheral band.

Still further in accordance with the first aspect, for instance, at least one lens of a vision system may be in the peripheral band, the at least one lens capturing images in a distal direction of the robotic arm.

Still further in accordance with the first aspect, for instance, electric insulation may be provided in the body.

In accordance with a second aspect, there is provided an interface for a robotic arm comprising: a body having a first axial face adapted to be connected to a distal face of a link of a robotic arm, a second axial face adapted to be connected to a proximal face of an end effector; a connection configuration for the interface to be fixed to the link and for the end effector to be fixed to the interface; circuitry embedded in the body; a circumferential surface defined between the first axial face and the second axial face; and at least one light source in the circumferential surface, the at least one light source connected to the circuitry to produce light.

Further in accordance with the second aspect, for instance, at least one of the light sources is in a lower portion of the circumferential surface so as to produce light in a downward direction.

Still further in accordance with the second aspect, for instance, at least one lens of a vision system may be in the circumferential surface.

Still further in accordance with the second aspect, for instance, the at least one lens is in a lower portion of the circumferential surface so as to capture images below the end effector.

Still further in accordance with the second aspect, for instance, the circumferential surface defines a flat surface, at least one of the lens being in the flat surface.

Still further in accordance with the second aspect, for instance, further including at least one interface button in the circumferential surface.

In accordance with a third aspect, there is provided a robot comprising: a robotic arm; an interface as described above, the interface being between the distal arm and an end effector.

Further in accordance with the third aspect, for instance, the end effector is a non-powered tool support.

Still further in accordance with the third aspect, for instance, the interface is non-electrically connected to the end effector.

DETAILED DESCRIPTION

Figure 1A:
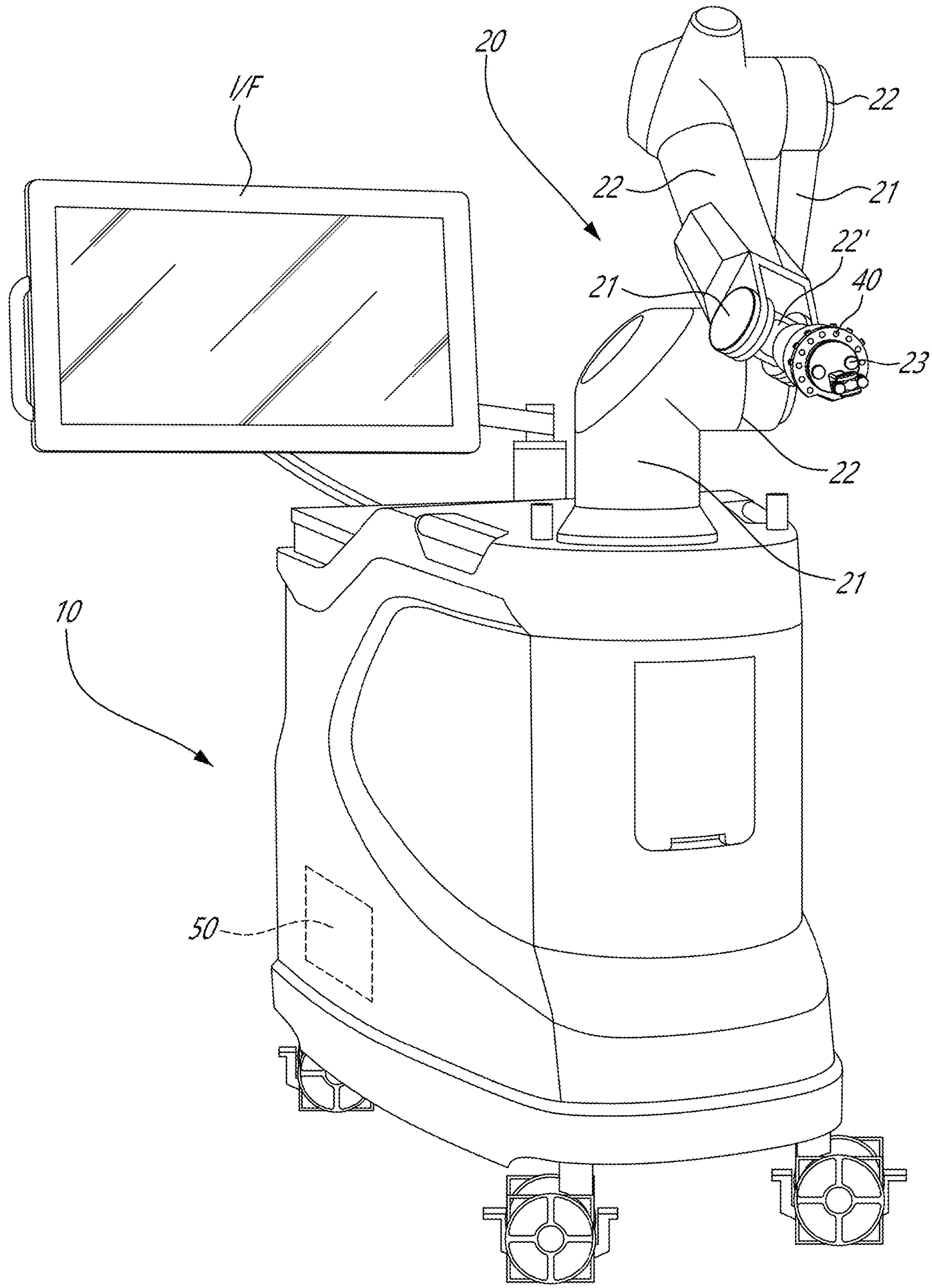
FIG. 1A is a perspective view of a surgical robot having a robot arm equipped with an electrical interface in accordance with the present disclosure.
Figure 1B:
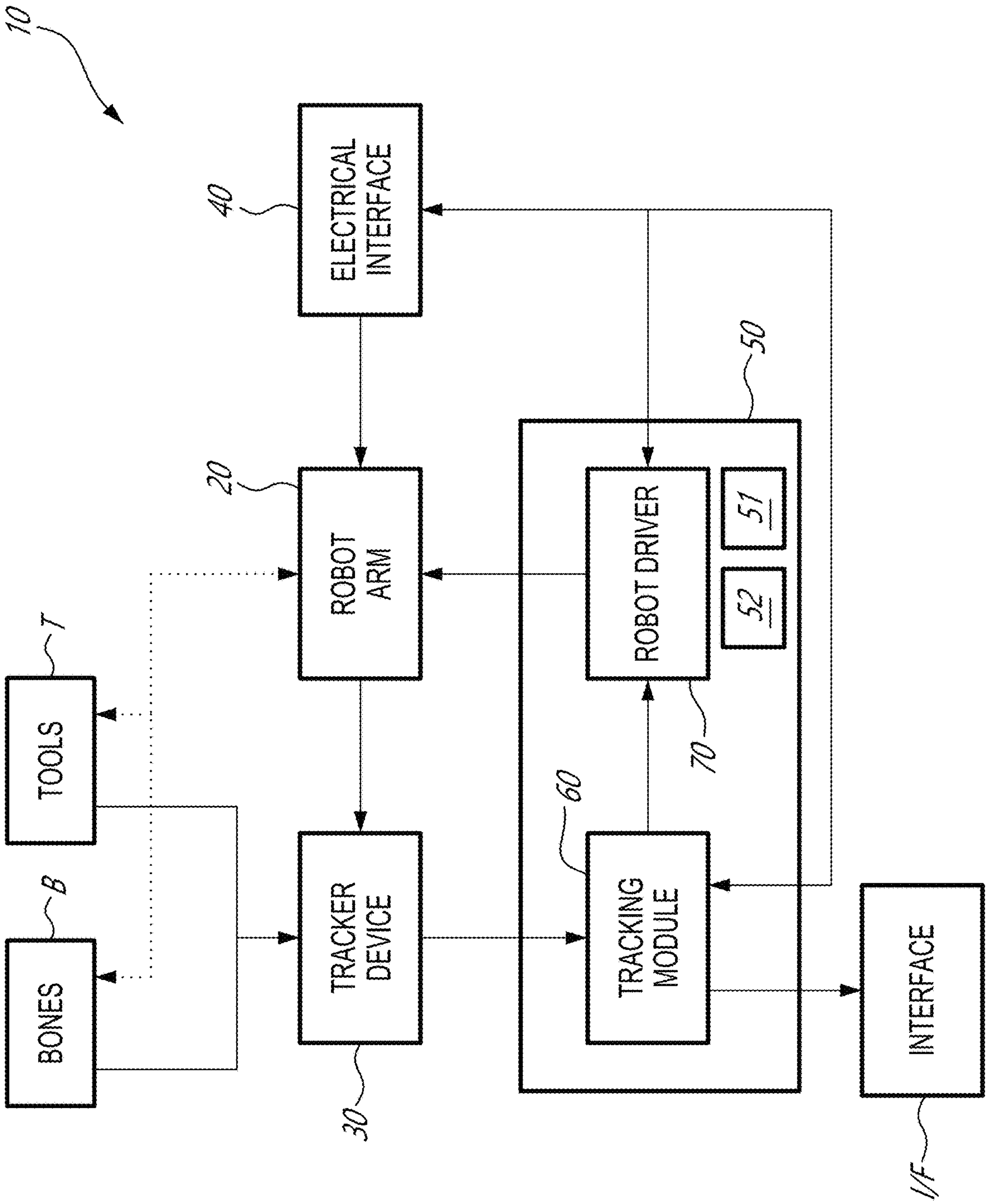
FIG. 1B is a block diagram of a robotized computer-assisted surgery (CAS) system featuring robot arm with the electrical interface of FIG. 1.

Referring to FIGS. 1A and 1B, a robotized computer-assisted surgery (CAS) system is generally shown at 10, and is used to provide surgery assistance to an operator. The robotized CAS system 10 may be robotized in a variant, and has, may have or may be used with a robot as shown by its one or more robot arms 20, a tracking device 30, a CAS controller 50, a tracking module 60, and a robot driver 70, or any combination thereof:

- The robot, shown by its robot arm 20 may optionally be present as the working end of the system 10. The robot arm 20 may be configured for collaborative/cooperative mode in which the operator may manipulate the robot arm 20 as controlled by the CAS controller 50. For example, the tooling end, also known as end effector, may be manipulated by the operator while supported by the robot arm 20. The robot arm 20 may be the coordinate measuring machine (CMM) of the robotized CAS system 10. The robot arm 20 could also be used to perform or guide bone alterations as planned by an operator and/or the CAS controller 50;
- The tracking device 30 is one example of a navigation system that may optionally be used to track the patient tissue, instruments, and the robot arm 20. For example, the tracking device 30 has the capacity to capture images, e.g., in video format, using camera technology similar such as depth cameras, with optional pattern projector, as described below, or may be a different imaging technology, to provide its video feed. For example, the tracking device is a Navitrack® system having the capacity to track retroreflective elements of tracker devices on the various objects (e.g., bones, tools, implants). The tracking device 30 may be said to be stationary. In some arrangements, the tracking device 30 includes multiple points of view. For example, the tracking device 30 may include or may be embodied by a head-mounted device worn by an operator, such as by the surgeon performing surgery. The head-mounted tracking device has the capacity to capture images. If present, the head-mounted device may have a display screen to provide data to the wearer, though this may be optional in an embodiment. The head-mounted tracking device may be used to provide a display in augmented/mixed and/or virtual reality to a user. The head-mounted tracking device may also be tasked with taking images of the surgery, with the images being used for the tracking of patient tissue (such as bones) and tools, for instance as a video feed. The head-mounted tracking device may also be used as an interface by which an operator may communicate commands to the robotic CAS system 10. The tracking device 30 may use ultrasounds as well.
- An electric interface 40 may be located at the working end of the robot arm 20. The electric interface 40 may be used to introduce functionalities to the robot arm 20, notably for interactions with the user, and/or to provide additional data acquisition.
- The CAS controller 50 includes the processor(s) and appropriate hardware and software to run a computer-assisted surgery procedure in accordance with one or more workflows. The CAS controller 50 may include or operate the tracking module 60, and/or the robot driver 70. As described hereinafter, the CAS controller 50 may also drive the robot arm 20 through a planned surgical procedure;
- The tracking module 60 is tasked with determining the position and/or orientation of the various relevant objects during the surgery procedure, such as the bone(s) B and tool(s) T, using data acquired by the robot arm 20 and/or by the tracking device 30, and/or obtained from the robot driver 70. The position and/or orientation may be used by the CAS controller 50 to control the robot arm 20 in a referential system;
- The robot driver 70 is tasked with powering or controlling the various joints of the robot arm 20, based on operator demands or on surgery planning.

Other components, devices, systems, may be present, such as surgical instruments and tools T, interfaces I/F such as displays, screens, computer station, servers, and like etc. Secondary robotized CAS systems may also be used for redundancy. The interfaces I/F may include one such interface as part of the base or station supporting the robot arm 20, as shown in FIG. 1A.

Referring to FIGS. 1A, 2, 3, 6 and 7, the robot 20 (referred to herein as robot 20 or robot arm 20) may have the robot arm stand from a base, for instance in a fixed relation relative to the operating-room (OR) table supporting the patient, whether it is attached or detached from the table. The robot arm 20 has a plurality of joints 21 and links 22, of any appropriate form, to support a tool head 23 that is used to perform various actions. In the illustrated embodiments, the tool head 23 is a clamp or like connection tool for supporting a tool T. The tool head 23 may be of other types as well, such as a cut guide and/or a drill guide, a registration pointer, etc. In any of the embodiments described herein, it is possible to use a tool interface 23' (FIG. 6) between the distal most-link 22 or electric interface 40/40' and the tool head 23. Hence, the tool head 23 may be connected to the tool interface 23', which itself is connected to the robot arm 20 or electric interface 40/40'. The tool interface 23' is a spacer-like device that may define a boundary between sterile zone and non-sterile zone. The tool interface 23' may also be the component to which the surgical drape (if present) is attached. In the subsequent paragraphs, even if the tool interface 23' is not mentioned, it could be present.

Any of the links 22, including a wrist or like distal-most link 22' (FIG. 7), may optionally incorporate a force/torque sensor for collaborative/cooperative control mode, in which an operator manipulates the robot arm 20. The robot arm 20 is shown being a serial mechanism, arranged for the tool head 23 to be displaceable in a desired number of degrees of freedom (DOF). For example, the robot arm 20 controls 6-DOF movements of the tool head, i.e., X, Y, Z in the coordinate system, and pitch, roll and yaw. Fewer or additional DOFs may be present. For simplicity, in some of the figures, only a fragmented illustration of the joints 21 and links 22 is provided, but more joints 21 of different types may be present to move the tool head 23 in the manner described above. The joints 21 are powered for the robot arm 20 to move as controlled by the CAS controller 50 in the six DOFs, and in such a way that the position and orientation of the tool head 23 in the coordinate system may be known, for instance by readings from encoders on the various joints 21, or from any integrated rotational joint sensing enabling rotation of the joints 21 to be quantified, and/or via tracking by the tracking device 30. Moreover, the tool head 23 may be calibrated relative to the robot arm 20, in such a way that the position and/or orientation of the tool head 23 in the referential system of surgery is known. Various techniques may be used to calibrate the tool head 23, as known in the art. Therefore, the powering of the joints is such that the tool head 23 of the robot arm 20 may execute precise movements, such as moving along a single direction in one translation DOF, or being restricted to moving along a plane, among possibilities. Such robot arms 20 are known, for instance as described in U.S. patent application Ser. No. 11/610,728, and incorporated herein by reference. Additionally, an inertial sensor unit may be on the robot arm 20 for the tracking of the end effector of the robot arm 10.

In a variant, the tool head 23 of robot arm 20 may be defined by a chuck or like tool interface, that is non-powered and that serves as a guide and/or support for tools T manipulated and/or supported by the operator (e.g., a surgeon, physician or like medical professional). Nevertheless, it is considered to equip the robot arm 20 with powered tools as tool head 23, such as a reamer (e.g., cylindrical, tapered), a reciprocating saw, a retractor, a laser rangefinder or light-emitting device (e.g., the indicator device of U.S. Pat. No. 8,882,777), laminar spreader depending on the nature of the surgery. The various tools may be part of a multi-mandible configuration or may be interchangeable, whether with human assistance, or as an automated process. The installation of a tool in the tool head may then require some calibration in order to track the installed tool in the X, Y, Z coordinate system of the robot arm 20. The tool head 23 of the robot arm 20 may also be a universal instrument adapter, which can be positioned by robot arm 20 relative to the surgical area in a desired orientation according to a surgical plan, such as a plan based on preoperative imaging. The universal instrument adapter may include a tool base, an extension arm, at the end of which a cutting guide is located. The cutting guide may be known as a cutting block, adapter block, etc. In an embodiment, the extension arm may have a first segment and second segment, though fewer or more segments may be present, so as to give a given orientation to the cutting guide relative to the tool head. The cutting guide may have a body defining a guide surface (e.g., cut slot), and pin holes. In an example, the cutting guide can be configured as a talus resection block for use in a total knee arthroplasty. Other configurations of the cutting guide may be used, such as with or without pin holes. Again, calibration steps may be performed if required to calibrate any end effector instrument.

In order to position the tool head 23 or like end effector of the robot arm 20 relative to the patient, the CAS controller 50 can manipulate the robot arm 20 automatically by the robot driver 70, or by a surgeon manually operating the robot arm 20 (e.g. physically manipulating, via a remote controller through the interface I/F) to move the end effector of the robot arm 20 to the desired location, e.g., a location called for by a surgical plan to align an instrument relative to the anatomy. When the surgeon manually operates the robot arm 20, it may be in a collaborative mode in which the robot arm 20 may sense forces applied to the robot arm 20 and actuate its joints 21 as a function of force vectors. Once aligned, a step of a surgical procedure can be performed.

The robot arm 20 may include sensors 25 in its various joints 21 and links 22. The sensors 25 may be of any appropriate type, such as rotary encoders, optical sensors, position switches, for the position and orientation of the end effector, and of the tool in the tool head 23 (e.g., cutting block) to be known. More particularly, the tracking module 60 may determine the position and orientation of the robot arm 20 in a frame of reference of the robot arm 20, such as by obtaining the position (x,y,z) and orientation (phi, theta, ro) of the tool from the robot driver 70 using the sensors 25 in the robot arm 20. Using the data from the sensors 25, the robot arm 20 may be the coordinate measuring machine (CMM) of the robotized CAS system 10, with a frame of reference (e.g., coordinate system, referential system) of the procedure being relative to the fixed position of the base of the robot 20. The sensors 25 must provide the precision and accuracy appropriate for surgical procedures. The coupling of tools to the robot arm 20 may automatically cause a registration of the position and orientation of the tools in the frame of reference of the robot arm 20, though steps of calibration could be performed. For example, when a cutting guide is coupled to the robot arm 20, a position and orientation of the guide surface may be registered for its subsequent tracking as the robot arm 20 moves in space. The geometry of the cutting guide is thus known, as well as the manner by which the cutting guide is coupled to the robot arm 20, to allow this automatic registration. Additional steps may be performed to register/calibrate the cutting guide, such as the contact with a probe, image processing, data entry, etc. The sensors 25 may include force/torque sensors for three axis of torque and three directions of forces, for example. Such sensors may be useful as part of the operation of a collaborative mode.

Figure 2:
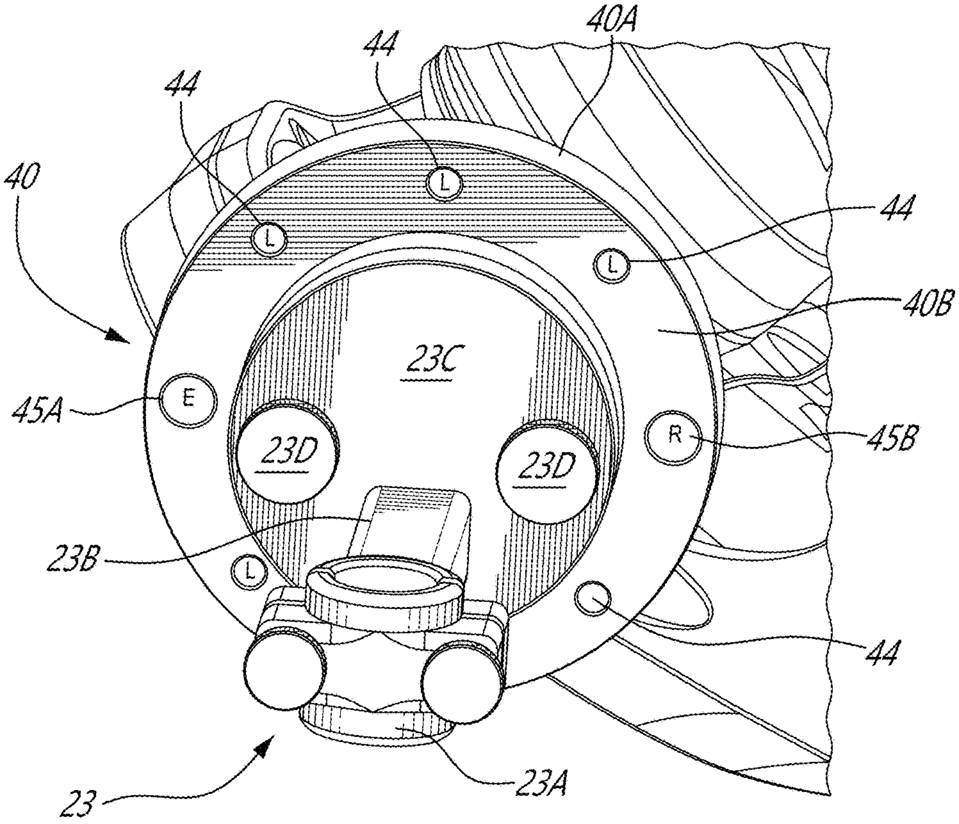
FIG. 2 is a perspective view showing an electrical interface for robot arm in accordance with a first variant, supporting a tool head.
Figure 3:
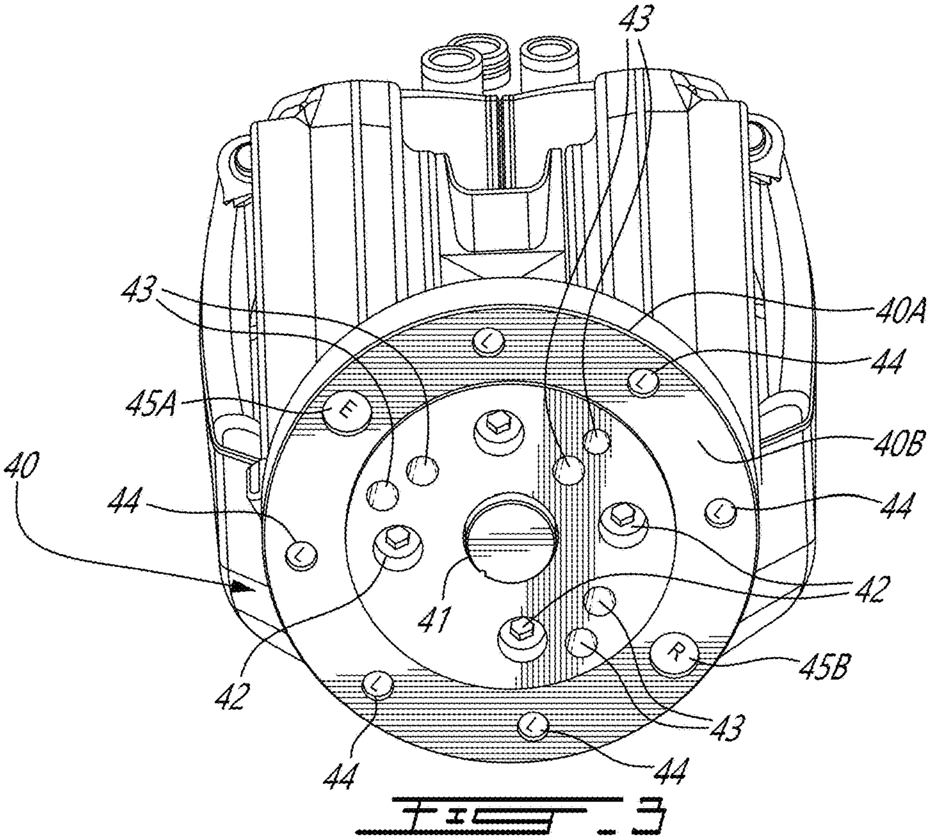
FIG. 3 is a perspective view of the electrical interface for robot arm of FIG. 2, without tool.
Figure 4:
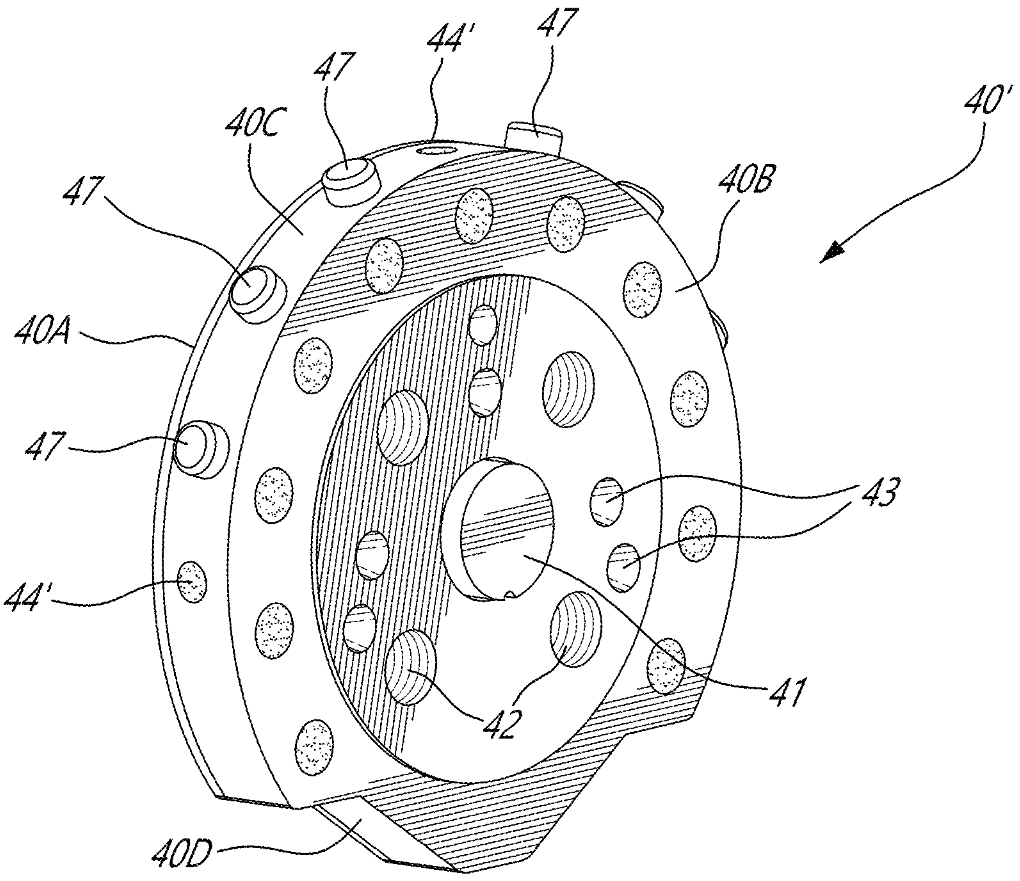
FIG. 4 is a perspective view showing an electrical interface for robot arm in accordance with a second variant.

Referring to FIGS. 2 and 3, an embodiment of the electrical interface 40 is illustrated. In an embodiment, the electrical interface 40 is connected directly to the wrist 22' (FIG. 7), and is between the wrist 22' or other distal face of the robotic arm 20, and the tool head 23 (FIG. 3) or other proximal face of the end effector including the tool interface 23' (FIG. 6) if present. The tool head 23 is shown as being a passive (i.e., non-powered) clamp 23A at the end of an arm 23B projecting from a base 23C, as an example among others. The electrical interface 40 may incorporate electrical insulation, to avoid any electrical interference with a tool supported by the tool head 23. In spite of the electrical insulation, the electrical interface 40 is powered to bring additional functionalities to the end of the distal end of the robot arm 20, as described below, including signaling capacity and data transmission. Accordingly, the electrical interface 40 may be layered internally, such as by having a shielding layer positioned distally relative to a printed-circuit board (PCB) or other circuitry embedded or located inside the electrical interface 40. The electrical interface 40 has any appropriate body shape. The electrical interface 40 is shown in FIGS. 2 and 3 as optionally having a disc-shaped (disk-shaped) body 40A, with a round geometry, through other geometries are contemplated (e.g., polygonal, square, oval, etc), one of which is described below. It can be observed that a dimension of the disc body 40A is greater than that of a base of the tool head 23 or like proximal face of the end effector, so as to define a peripheral or like surrounding surface 40B that projects beyond the base 23C of the tool head 23. Surface 40B may lie in an axial plane. This could be achieved in other ways, such as by having a different geometry. In an embodiment, the base 23C is generally of similar shape and size (e.g., diameter) as that of the wrist 22'. Accordingly, the disc body 40A may act as a flange, and may also serve as a support or interface for a drape. In a variant, a drape is connected to a rear surface of the disc body 40A. The electrical interface 40 may be powered via the robot arm 20, or by wires internally routed into the robot arm 20 or exterior to the robot arm 20. The wiring may be proximally located relative to the drape, if present. As an alternative, the electrical interface 40 may include a battery, so as to be wireless and battery operated. Accordingly, the electrical interface 40 may include a telecommunications unit, using any appropriate telecommunications protocol (e.g., wi-fi, Bluetooth®, etc).

The peripheral surface 40B may be said to be a distal surface, as it is located toward the distal end of the robot arm 20. Moreover, the peripheral surface 40B may be normal to a rotational axis of the wrist 20' as a possibility. Accordingly, the peripheral surface 40B faces distally, toward the tool head 23. In an embodiment, the peripheral surface 40B is substantially flat, though this is optional.

Depending on the nature of the tool head 23, the electrical interface 40 may have a mating connector 41 as part of a connection configuration. The mating connector 41 is shown as being a male connector, and/or may have cylindrical shape or any other projecting shape, but other configurations are possible, including a female connector. Moreover, even though the geometry of the mating connector 41 is regular and uniform, the mating connector 41 could have a clocking feature to ensure a unique complementary positioning of the tool head 23 on the electrical interface 40.

Attachment bore(s) 42, such as threaded bores, may be circumferentially distributed around the mating connector 41 if present, or may be at other locations, and may also be part of the connector configuration. The attachment bore(s) 42 may be used to secure a tool such as the tool head 23 to the electrical interface 40. Accordingly, some compatibility is required between the mating connector 41 and/or attachment bore(s) 42, for tools to be attached to the electrical interface 40. Moreover, different patterns and configurations of attachment bores 42 may be present as part of the connector configuration, for the electrical interface 40 to be compatible with different tool types.

Alignment features 43 may optionally be present, for example if no other clocking feature is present, and may be part of the connector configuration. The alignment features 43 may be circumferentially distributed around the mating connector 41 if present, or may be at other locations. In the illustrated embodiment, the alignment features 43 may be conical holes and/or conical projections, matingly engaged with complementary features on the tool head 23. The alignment features 43 are used to ensure a precise positioning engagement of the tool head 23, for example by removing any possible play between the tool head 23 and the electrical interface 40 once connected, provided the fastener(s) received in the attachment bore(s) 42 is suitably tightened, such as threaded members with knobs 23D on the tool head 23 (FIG. 2). The alignment features 43 contribute to the stability of the assembly, and to the precision of the positioning of the tool head 23 in the referential system, as the geometrical relation between the tool head 23 and the electrical interface 40 is predictable and reproducible. The alignment features 43 may be factor in the improvement of surgical precision.

Light source(s) 44 may be located on the peripheral surface 40B. For example, the light sources 44 are embedded in the disc body 40A so as not to project beyond a surface of the peripheral surface 40B, but this is merely optional. As the light sources 44 are on the peripheral surface 40B, their light is projected in a distal direction, generally along an axis of the wrist 22'. As the wrist 22' is in the vicinity of the surgical site, and as the wrist 22' may often support a tool (e.g., tool head 23) that is along the rotation axis of the wrist 22', the light source(s) 44 is (are) strategically positioned to assist in providing light at the surgical site. As observed, there may be more than one light source 44, with some of the light sources 44 located in a lower half of the disc body 40A, and some of the light sources 44 located in an upper half of the disc body 40A. Depending on the source of ambient light projected onto the surgical site, the location of the light sources 44 on the lower half and upper half may ensure that a zone that is otherwise shaded by the tool head 23 is illuminated (lights may be in all four quadrants if the peripheral surface 40B extends for more than 270 degrees. In a variant, the light source(s) 44 is (are) light-emitted diodes, and may be selected based on light spectrum requirements. Other types of light sources could be used. Thus, the light source(s) 44, if present, enable the electrical interface 40 to provide focused lighting on the operated area.

Still referring to FIGS. 2 and 3, an emitter 45A and a receiver 45B may also be located on the peripheral surface 40B of the disc body 40A. The emitter 45A and the receiver 45B work as a pair to perform detection, such as ranging, proximity sensing, tracking. The emitter 45A and the receiver 45B are shown as a separate pair, but the emitter 45A and the receiver 45B may be grouped in a single location on the peripheral surface 40B, or multiple pairs may also be present. The technology used by the emitter 45A and receiver 45B may be of any type. For example, the technology can be based on a reflection of light, a laser, a sound or an ultrasound or other. The emitter 45A and receiver 45B are on the peripheral surface 40B, giving them a close-up point of view of the surgical site, aligned with the axis of the wrist 22'.

Referring to FIGS. 4-7, another embodiment of the electrical interface is illustrated as 40'. The electrical interface 40' shares some features with the electrical interface 40 of FIGS. 2 and 3, and like reference numerals will indicate like components. The electrical interface 40' is also connected directly to the wrist 22' (FIGS. 6 and 7), and is between the wrist 22' and the tool head 23 (FIG. 6) or tool interface 43' if present, again the tool head 23 may be a passive (i.e., non-powered) clamp 23A, as an example among others. The electrical interface 40' may also incorporate electrical insulation, to avoid any electrical interference with a tool supported by the tool head 23. In spite of the electrical insulation, the electrical interface 40' is powered to bring additional functionalities to the end of the distal end of the robot arm 20, as described below, including data transmission, signaling. The electrical interface 40' may include a shielding layer positioned distally relative to a printed-circuit board (PCB) or other electric/electronic components.

The electrical interface 40' has any appropriate body shape. The electrical interface 40' resembles the electrical interface 40 in that it is generally disc-shaped (disk-shaped) body 40A, but with truncated portions in the outer periphery 40C, defining optional flat support surfaces 40D in the outer periphery 40C. As observed, the support surfaces 40D may face downwardly. The body 40A may also have width dimensions greater than that of a base of the tool head 23, so as to define the peripheral surface 40B that projects beyond the base 23C of the tool head 23. The body 40A may thus be viewed as a flange relative to the wrist 22'. The body 40A may serve as a support or interface for a drape. In a variant, a drape is connected to a rear surface of the body 40A.

The electrical interface 40' may be powered via the robot arm 20, or by wires internally routed into the robot arm 20 or exterior to the robot arm 20. The wiring may be proximally located relative to the drape, if present. As an alternative, the electrical interface 40' may include a battery, so as to be wireless and battery operated. Accordingly, the electrical interface 40 may include a telecommunications unit, using any appropriate telecommunications protocol (e.g., wi-fi, Bluetooth®, etc).

The peripheral surface 40B may be said to be a distal surface, as it is located toward the distal end of the robot arm 20. Moreover, the peripheral surface 40B may be normal to a rotational axis of the wrist 20' as a possibility. Accordingly, the peripheral surface 40B faces distally, toward the tool head 23. In an embodiment, the peripheral surface 40B is substantially flat, though this is optional.

Depending on the nature of the tool head 23, the electrical interface 40' may have a mating connector 41, as part of a connector configuration. The mating connector 41 is shown as being a male connector, or cylindrical shape, but other configurations are possible, including a female connector. Moreover, even though the geometry of the mating connector 41 is regular and uniform, the mating connector 41 could have a clocking feature to ensure a unique complementary positioning of the tool head 23 on the electrical interface 40'. This is visible in the various embodiments in the form of a keyway on the mating connector 41.

Attachment bore(s) 42, e.g., threaded bores, may be circumferentially distributed around the mating connector 41 if present, or may be at other locations, and may be part of the connector configuration. The attachment bore(s) 42 may be used to secure a tool such as the tool head 23 to the electrical interface 40'. Some compatibility is required between the mating connector 41 and/or attachment bore(s) 42, for tools to be attached to the electrical interface 40'. Moreover, different patterns and configurations of attachment bores 42 may be present, for the electrical interface 40' to be compatible with different tool types.

Figure 6:
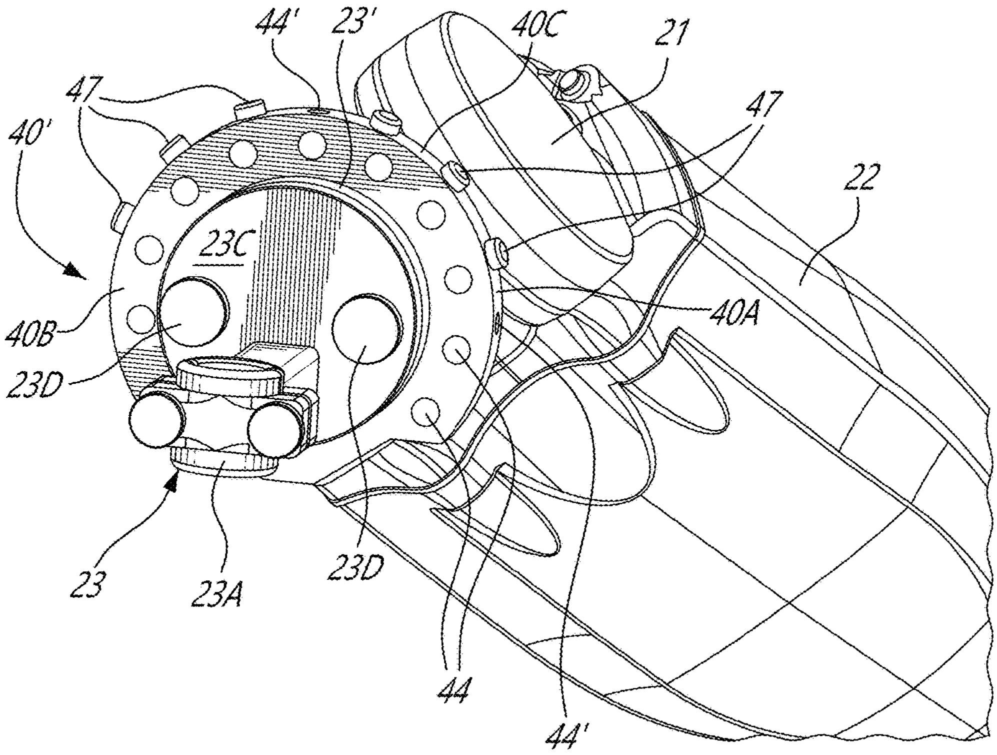
FIG. 6 is a perspective view of the electrical interface of FIG. 4 on a robot arm.

Alignment features 43 may optionally be present, as part of the connector configuration. The alignment features 43 may be circumferentially distributed around the mating connector 41 if present, or may be at other locations. The alignment features 43 may be in a non-symmetrical pattern, to create a unique orientation connection correspondence between the electrical interface 40' and the tool head 23 (or any other tool to be connected to the electrical interface 40'. In the illustrated embodiment, the alignment features 43 may be conical holes and/or conical projections, matingly engaged with complementary features on the tool head 23. The alignment features 43 are used to ensure a precise positioning engagement of the tool head 23, for example by removing any possible play between the tool head 23 and the electrical interface 40' once connected, provided the fastener(s) received in the attachment bore(s) 42 is suitably tightened, such as threaded members with knobs 23D on the tool head 23 (FIG. 6). The alignment features 43 contribute to the stability of the assembly, and to the precision of the positioning of the tool head 23 in the referential system, as the geometrical relation between the tool head 23 and the electrical interface 40' is predictable and reproducible.

Light source(s) 44 may be located on the peripheral surface 40B. For example, the light sources 44 are embedded in the disc body 40A so as not to project beyond a surface of the peripheral surface 40B, but this is merely optional. Other light sources 44' may be provided on the peripheral surface 40C and/or on the flat support surfaces 40D, and may be selectively turned on an off (such light sources 44' may also be in the electrical interface 40). These light sources 44' may be in every quadrant of the electrical interface 40. As the light sources 44 are on the peripheral surface 40B, their light is projected in a distal direction, generally along an axis of the wrist 22'. As the wrist 22' is in the vicinity of the surgical site, and as the wrist 22' may often support a tool (e.g., tool head 23) that is along the rotation axis of the wrist 22', the light source 44 and 44' are strategically positioned to assist in providing light at the surgical site. As observed, there may be more than one light source 44, with some of the light sources 44 located in a lower half of the disc body 40A, and some of the light sources 44 located in an upper half of the disc body 40A. Depending on the source of ambient light projected onto the surgical site, the location of the light sources 44 and 44' on the lower half and upper half may ensure that a zone that is otherwise shaded by the tool head 23 is illuminated. In a variant, the light source 44 and/or 44' are light-emitted diodes, and may be selected based on light spectrum requirements. Other types of light sources could be used. Thus, the light sources 44 and 44', if present, enable the electrical interface 40 to provide focused lighting on the operated area.

Figure 5:
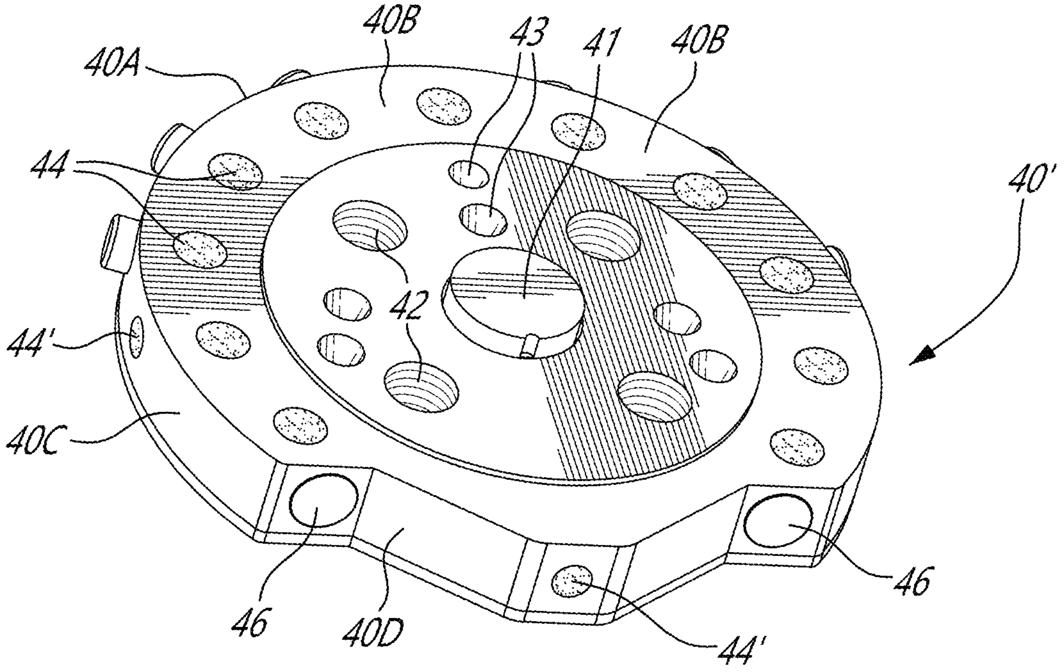
FIG. 5 is another perspective view of the electrical interface for robot arm of FIG. 4.
Figure 7:
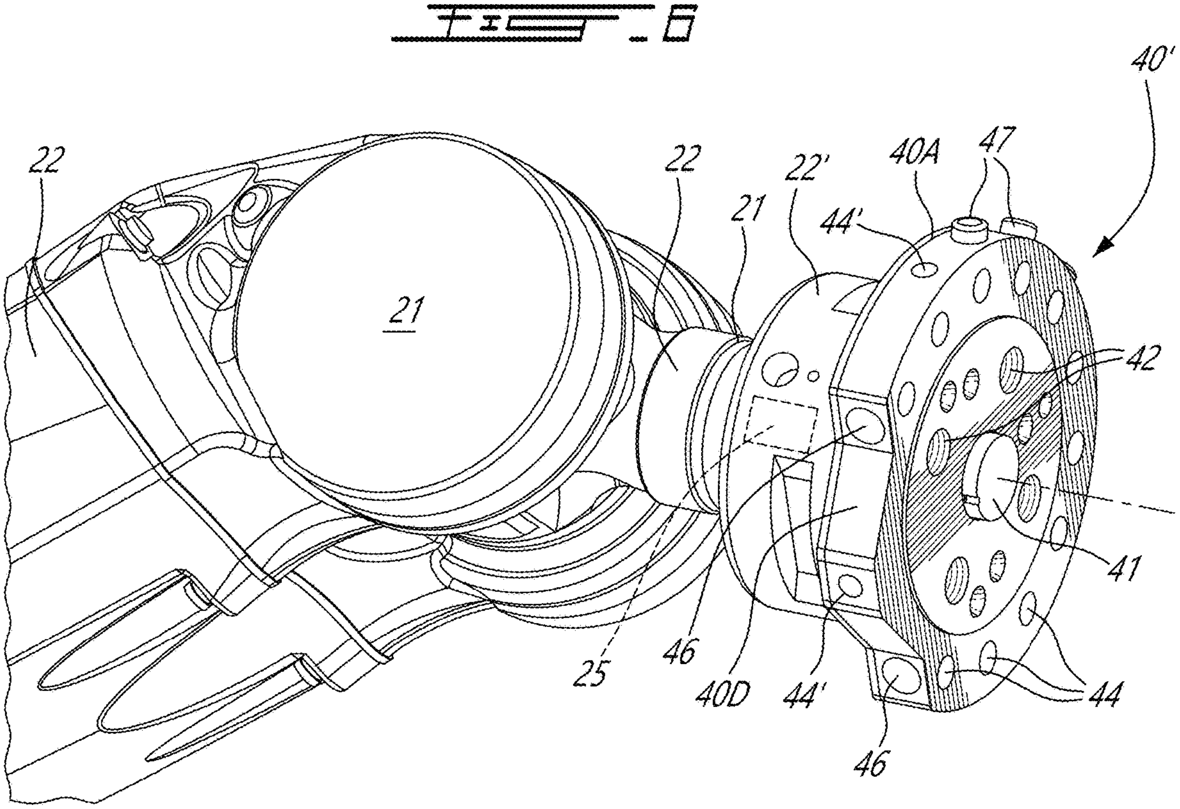
FIG. 7 is another perspective view of the assembly of the electrical interface and the robot arm of FIG. 6.

Referring to FIGS. 5 and 7, a vision system may be provided in the electrical interface 40', as shown by the presence of one or more lenses 46, located on the flat support surfaces 40C of the body 40A, but potentially located elsewhere, including on the peripheral surface 40B. The vision system may be used to capture images, video feed, and may also be used for other functions such ranging, proximity sensing, tracking. The lenses 46 are shown as a pair, so as to enable triangulation tracking, depth camera functionality, such as in the infrared spectrum.

Buttons 47 may be provided on the electrical interface 40' (and also in the electrical interface 40 though not shown). The buttons 47 may be mechanical and thus connected to switches within the electrical interface 40'. Other technologies can be used, include capacitive sensing. The buttons 47 may strategically be positioned on the periphery 40C of the body 40A, so as to be readily accessible. In a variant, the buttons 47 may be configured by a user of the robot arm 20 to perform selected functions, such as some functions related to the operation of the electrical interface 40' (e.g., turning lights 44 on/off), or optionally functions associated with the surgical workflow, in a manner similar to a keyboard, mouse, etc. The buttons 47 may be taught some functions.

Accordingly, the electrical interface 40' may use the vision system to perform various functions. For instance, the electrical interface 40' may be used to facilitate patient landmark registration, by capturing images of such bone landmarks in proximity to the patient. For example, the captured images of the vision system of the electrical interface 40' may be used to monitor the relative position of the patient in relation to the instrumentation in real time throughout the surgery, from a privileged proximal point of view, which may result in enhanced accuracy.

Both electrical interfaces 40 and 40' are configured to be placed in between a link of the robotic arm 20, such as the wrist 22', and the end effector (including any passive or active component, tool) that is at the distal end of the robotic arm 20. Accordingly, the electrical interfaces 40 and 40' may be retrofitted to existing systems, and their connector configurations may be disposed depending on the type of robotic arm 20/end effector. Moreover, their thinness gives the electric interfaces 40 and 40' a small footprint, for example in comparison to other interfaces and tracking camera.

Referring to FIG. 1B, the tracking device 30 may optionally be used to track the patient tissue, instruments, and the robot arm 20. The tracking device 30 may include the vision system that is on the electrical interface 40'. In an embodiment, the tracking device 30 includes a Navitrack® system having the capacity to track retroreflective elements of tracker devices on the various objects (e.g., bones, tools, implants). As such, and in other variants, the tracking device 30 may have the capacity to capture images, e.g., in video format, using camera technology similar such as depth cameras, with optional pattern projector, as described below, or may be a different imaging technology, to provide its video feed. In some arrangements, the tracking device 30 includes multiple separate image capture devices from different points of view, including the lens(es) 46 of the vision system of the electrical interface 40'. The tracking device 30 may include or may be embodied by a head-mounted device worn by an operator, such as by the surgeon performing surgery. If present, the head-mounted device may have a display screen to provide data to the wearer, though this may be optional in an embodiment.

The tracking device 30 (including the vision system of the electrical interface 40') may produce structured light illumination for tracking objects with structured light 3D imaging. In structured light illumination, a portion of the objects is illuminated with one or multiple patterns from a pattern projector or like light source. Structured light 3D imaging is based on the fact that a projection of a line of light from the pattern projector onto a 3D shaped surface produces a line of illumination that appears distorted as viewed from perspectives other than that of the pattern projector. Accordingly, imaging such a distorted line of illumination allows a geometric reconstruction of the 3D shaped surface. Imaging of the distorted line of illumination is generally performed using one or more cameras (including appropriate components such as e.g., lens(es), aperture, image sensor such as CCD, image processor) which are spaced apart from the pattern projector so as to provide such different perspectives, e.g., triangulation perspective. In some embodiments, the pattern projector is configured to project a structured light grid pattern including many lines at once as this allows the simultaneous acquisition of a multitude of samples on an increased area. In these embodiments, it may be convenient to use a pattern of parallel lines. However, other variants of structured light projection can be used in some other embodiments.

The structured light grid pattern can be projected onto the surface(s) to track using the pattern projector. In some embodiments, the structured light grid pattern can be produced by incoherent light projection, e.g., using a digital video projector, wherein the patterns are typically generated by propagating light through a digital light modulator. Examples of digital light projection technologies include transmissive liquid crystal, reflective liquid crystal on silicon (LCOS) and digital light processing (DLP) modulators. In these embodiments, the resolution of the structured light grid pattern can be limited by the size of the emitting pixels of the digital projector. Moreover, patterns generated by such digital display projectors may have small discontinuities due to the pixel boundaries in the projector. However, these discontinuities are generally sufficiently small that they are insignificant in the presence of a slight defocus. In some other embodiments, the structured light grid pattern can be produced by laser interference. For instance, in such embodiments, two or more laser beams can be interfered with one another to produce the structured light grid pattern wherein different pattern sizes can be obtained by changing the relative angle between the laser beams.

The pattern projector may emit light that is inside or outside the visible region of the electromagnetic spectrum. For instance, in some embodiments, the emitted light can be in the ultraviolet region and/or the infrared region of the electromagnetic spectrum such as to be imperceptible to the eyes of the medical personnel. In these embodiments, however, the medical personnel may be required to wear protective glasses to protect their eyes from such invisible radiations. As alternatives to structured light, the tracking device 30 may also operate with laser rangefinder technology or triangulation, as a few examples among others.

The tracking device 30 may consequently include the cameras to acquire backscatter images of the illuminated portion of objects. Hence, the cameras capture the pattern projected onto the portions of the object. The cameras are adapted to detect radiations in a region of the electromagnetic spectrum that corresponds to that of the patterns generated by the light projector. As described hereinafter, the known light pattern characteristics and known orientation of the pattern projector relative to the cameras, are used by the tracking module 60 to generate a 3D geometry of the illuminated portions, using the backscatter images captured by the camera(s). Although a single camera spaced form the pattern projector can be used, using more than one camera may increase the field of view and increase surface coverage, or precision via triangulation.

The tracking device 30 may also have one or more filters integrated into either or both of the cameras to filter out predetermined regions or spectral bands of the electromagnetic spectrum. The filter can be removably or fixedly mounted in front of any given camera. For example, the filter can be slidably movable into and out of the optical path of the cameras, manually or in an automated fashion. In some other embodiments, multiple filters may be periodically positioned in front of a given camera in order to acquire spectrally resolved images with different spectral ranges at different moments in time, thereby providing time dependent spectral multiplexing. Such an embodiment may be achieved, for example, by positioning the multiple filters in a filter wheel that is controllably rotated to bring each filter in the filter wheel into the optical path of the given one of the camera in a sequential manner.

More specifically, the filter can be used to provide a maximum contrast between different materials which can improve the imaging process and more specifically the soft tissue identification process. For example, in some embodiments, the filter can be used to filter out bands that are common to backscattered radiation from typical soft tissue items, the surgical structure of interest, and the surgical tool(s) such that backscattered radiation of high contrast between soft tissue items, surgical structure and surgical tools can be acquired. Additionally, or alternatively, where white light illumination is used, the filter can includes band pass filters configured to let pass only some spectral bands of interest. For instance, the filter can be configured to let pass spectral bands associated with backscattering or reflection caused by the bones, the soft tissue while filtering out spectral bands associated with specifically colored items such as tools, gloves and the like within the surgical field of view. Other methods for achieving spectrally selective detection, including employing spectrally narrow emitters, spectrally filtering a broadband emitter, and/or spectrally filtering a broadband imaging detector, can also be used.

Referring to FIGS. 1A and 1B, the CAS controller 50 is shown in greater detail relative to the other components of the robotized CAS system 10. The CAS controller 50 has a processor unit 51 (one or more processors) and a non-transitory computer-readable memory 52 communicatively coupled to the processing unit 51 and configured for executing computer-readable program instructions executable by the processing unit 51 to perform some functions, such as tracking the patient tissue and tools, using the camera feed from the tracking device 30. The CAS controller 50 may also control the movement of the robot arm 20. The robotized CAS system 10 may comprise various types of interfaces I/F, for the information to be provided to the operator. In addition to the tracking device 30, the interfaces I/F may include a monitor and/or screens including wireless portable devices (e.g., phones, tablets), audio guidance, LED displays, among many other possibilities. For example, the interface D includes a graphic-user interface (GUI) operated by the system 10. The CAS controller 50 may drive the robot arm 20 in performing the surgical procedure based on the surgery planning achieved preoperatively. The CAS controller 50 may run various modules, in the form of algorithms, code, non-transient executable instructions, etc, in order to operate the CAS system 10 in the manner described herein. The CAS controller 50 may be part of any suitable processor unit(s), such as a personal computer or computers including laptops and desktops, tablets, server, cloud, etc.

The tracking module 60 may be a subpart of the CAS controller 50, or an independent module or system. The tracking module 60 receives from the tracking device 30 (if present) the video feed of the surgical scene, e.g., as backscatter images of the objects. In an embodiment, as the system 10 performs real-time tracking, the video images and the orientation data are synchronized, as they are obtained and processed simultaneously. Other processing may be performed to ensure that the video footage and the orientation data are synchronized.

The tracking module 60 processes the video images to track one or more objects, such as a bone, an instrument, etc. The tracking module 60 may determine the relative position of the objects, and segment the objects within the video images. In a variant, the tracking module 60 may process the video images to track a given portion of an object, that may be referred to as a landmark.

The tracking module 60 may also be provided with models of the objects to be tracked. For example, the tracking module 60 may track bones and tools, and hence uses virtual bone models and tool models. The bone models may be acquired from pre-operative imaging (e.g., MRI, CT-scans), for example in 3D or in multiple 2D views, including with 2D X-ray to 3D bone model technologies. The virtual bone models may also include some image processing done preoperatively, for example to remove soft tissue or refine the surfaces that will be exposed and tracked. The virtual bone models may be of greater resolution at the parts of the bone that will be tracked during surgery, such as the knee articulation in knee surgery. The bone models may also carry additional orientation data, such as various axes (e.g., longitudinal axis, mechanical axis, etc). The bone models may therefore be patient specific. It is also considered to obtain bone models from a bone model library, with the data obtained from the video images used to match a generated 3D surface of the bone with a bone from the bone atlas. The virtual tool models may be provided by the tool manufacturer, or may also be generated in any appropriate way so as to be a virtual 3D representation of the tool(s).

In a variant, the tracking module 60 may generate 3D models using the video images. For example, if the tracking module 60 can have video images of a tool, from 360 degrees, it may generate a 3D model that can be used for subsequent tracking. This intraoperative model may or may not be matched with pre-existing or pre-operative model of the tool.

Additional data may also be available, such as tool orientation (e.g., axis data and geometry). By having access to bone and tool models, the tracking module 60 may recognize an object in the image processing and/or may obtain additional information, such as the axes related to bones or tools. The image processing by the tracking module 60 may be assisted by the presence of the models, as the tracking module 60 may match objects from the video images with the virtual models.

Accordingly, the electrical interface 40 and 40' may be generally described as being an interface for a robotic arm that may have a body having a first axial face adapted to be connected to a distal face of a link of a robotic arm, a second axial face adapted to be connected to a proximal face of an end effector, the second axial face having a geometry differing from a geometry of the proximal face of the end effector so as to define a peripheral band in the second axial face, the peripheral band facing distally; a connection configuration for the interface to be fixed to the link and for the end effector to be fixed to the interface; circuitry embedded in the body; and at least one light source in the peripheral band, the at least one light source connected to the circuitry to produce light in a distal direction of the robotic arm.

The electrical interface 40 and 40' may alternatively be described as An interface for a robotic arm having a body having a first axial face adapted to be connected to a distal face of a link of a robotic arm, a second axial face adapted to be connected to a proximal face of an end effector; a connection configuration for the interface to be fixed to the link and for the end effector to be fixed to the interface; circuitry embedded in the body; a circumferential surface defined between the first axial face and the second axial face; and at least one light source in the circumferential surface, the at least one light source connected to the circuitry to produce light.

The invention claimed is:

1. An interface for a robotic arm comprising:

a body having a first axial face adapted to be connected to a distal face of a link of a robotic arm, a second axial face adapted to be connected to a proximal face of an end effector, the second axial face having a geometry differing from a geometry of the proximal face of the end effector so as to define a peripheral band in the second axial face, the peripheral band facing distally, the peripheral band extending around the proximal face of the end effector for at least 270 degrees;

a connection configuration for the interface to be fixed to the link and for the end effector to be fixed to the interface;

circuitry embedded in the body; and at least one light source in the peripheral band, the at least one light source connected to the circuitry to produce light in a distal direction of the robotic arm.

2. The interface according to claim 1, wherein the peripheral band extends around the proximal face of the end effector for 360 degrees.

3. The interface according to claim 1, wherein the interface has a plurality of the light source, at least one of the light sources being located in each quadrant of the peripheral band.

4. The interface according to claim 1, further including at least one lens of a vision system in the peripheral band, the at least one lens capturing images in a distal direction of the robotic arm.

5. The interface according to claim 1, further including electric insulation in the body.

6. The interface according to claim 1, further including a circumferential surface defined between the first axial face and the second axial face; and at least one light source in the circumferential surface, the at least one light source connected to the circuitry to produce light.

7. A robot comprising:

a robotic arm;

an interface according to claim 1, the interface being between a distal arm and an end effector.

8. The robot according to claim 7, wherein the end effector is a non-powered tool support.

9. The robot according to claim 8, wherein the interface is non-electrically connected to the end effector.

10. An interface for a robotic arm comprising:

a body having a first axial face adapted to be connected to a distal face of a link of a robotic arm, a second axial face adapted to be connected to a proximal face of an end effector;

a connection configuration for the interface to be fixed to the link and for the end effector to be fixed to the interface;

circuitry embedded in the body;

a circumferential surface defined between the first axial face and the second axial face; and at least one light source in the circumferential surface, the at least one light source connected to the circuitry to produce light.

11. The interface according to claim 10, wherein at least one of the light sources is in a lower portion of the circumferential surface so as to produce light in a downward direction.

12. The interface according to claim 10, further including at least one lens of a vision system in the circumferential surface.

13. The interface according to claim 12, wherein the at least one lens is in a lower portion of the circumferential surface so as to capture images below the end effector.

14. The interface according to claim 12, wherein the circumferential surface defines a flat surface, at least one of the lens being in the flat surface.

15. The interface according to claim 10, further including at least one interface button in the circumferential surface.

16. The interface according to claim 10, wherein the second axial face having a geometry differing from a geometry of the proximal face of the end effector so as to define a peripheral band in the second axial face, the peripheral band facing distally, at least one light source in the peripheral band, the at least one light source connected to the circuitry to produce light in a distal direction of the robotic arm.

17. The robot according to claim 10, wherein the interface is non-electrically connected to the end effector.

18. A robot comprising:

a robotic arm;

an interface according to claim 10, the interface being between a distal arm and an end effector.

19. The robot according to claim 18, wherein the end effector is a non-powered tool support.

20. An interface for a robotic arm comprising:

a body having a first axial face adapted to be connected to a distal face of a link of a robotic arm, a second axial face adapted to be connected to a proximal face of an end effector, the second axial face having a geometry differing from a geometry of the proximal face of the end effector so as to define a peripheral band in the second axial face, the peripheral band facing distally;

a connection configuration for the interface to be fixed to the link and for the end effector to be fixed to the interface;

circuitry embedded in the body; and a plurality of light sources in the peripheral band, the plurality of the light sources connected to the circuitry to produce light in a distal direction of the robotic arm, each quadrant of the peripheral band having at least one of the light sources located therein.

21. An interface for a robotic arm comprising:

a body having a first axial face adapted to be connected to a distal face of a link of a robotic arm, a second axial face adapted to be connected to a proximal face of an end effector, a circumferential surface defined between the first axial face and the second axial face, the second axial face having a geometry differing from a geometry of the proximal face of the end effector so as to define a peripheral band in the second axial face, the peripheral band facing distally;

a connection configuration for the interface to be fixed to the link and for the end effector to be fixed to the interface;

circuitry embedded in the body;

at least one circumferential light source in the circumferential surface, the at least one circumferential light source connected to the circuitry to produce light; and at least one peripheral light source in the peripheral band, the at least one peripheral light source connected to the circuitry to produce light in a distal direction of the robotic arm.

* * * * *